United States Patent

Kieturakis

[19]

[11] Patent Number: 6,036,713
[45] Date of Patent: Mar. 14, 2000

[54] INSTRUMENTS AND METHODS FOR MINIMALLY INVASIVE VASCULAR PROCEDURES

[75] Inventor: Maciej J. Kieturakis, San Carlos, Calif.

[73] Assignee: Archimedes Surgical, Inc., Menlo Park, Calif.

[21] Appl. No.: 08/786,986

[22] Filed: Jan. 23, 1997

Related U.S. Application Data

[60] Provisional application No. 60/011,137, Jan. 24, 1996.
[51] Int. Cl.[7] ................................................. A61B 17/00
[52] U.S. Cl. ........................... 606/190; 606/191; 606/159
[58] Field of Search .................. 606/207, 190, 606/96, 191, 192, 204, 159

[56] References Cited

U.S. PATENT DOCUMENTS

| | | | |
|---|---|---|---|
| 5,603,720 | 2/1997 | Kieturakis | 606/191 |
| 5,667,480 | 9/1997 | Knight et al. | 606/190 |
| 5,759,150 | 6/1998 | Konou et al. | 606/190 |

*Primary Examiner*—Michael Buiz
*Assistant Examiner*—Tan-Uyen T. Ho
*Attorney, Agent, or Firm*—Townsend and Townsend and Crew LLP

[57] ABSTRACT

A 360° dissection instrument and method for accomplishing an atraumatic blunt dissection of connective tissues in 360° around the circumference of a saphenous vein and branch veins to facilitate a minimally invasive harvesting of the vein. The 360° pulsable dissector has an elongate body with a distal dissecting surface that is progressively "circumferential" or "wrapped" around an axial vessel-receiving passageway or channel. The dissecting surface includes a longitudinal gap that has a reduced transverse dimension in the proximal direction to funnel branch veins through the gap. The wrapped dissecting surface includes an "active" periphery incorporating a pulsable expansion structure of elastomeric material having and interior pressurizable chamber. An inflation lumen in the dissector body communicates with a pressure source and a pulse-control mechanism. A single pulse will move the expansion structure in a "pulse cycle" through an "expansion phase" and a "contraction" phase at pulse intervals ranging from 1/second to 100/second. In one embodiment, endoscopic viewing means are provided within the body of the dissector.

21 Claims, 10 Drawing Sheets

INSTRUMENTS AND METHODS FOR MINIMALLY INVASIVE VASCULAR PROCEDURES

CROSS-REFERENCE TO RELATED APPLICATIONS

This application derives priority from provisional application Ser. No. 60/011,137, filed Jan. 24, 1996, the complete disclosure of which is incorporated herein by reference.

This application is related to the following co-pending and commonly invented U.S. Patent Applications, all of which are incorporated by this reference herein: U.S. Ser. No. 08/316,290, filed Sep. 30, 1994; U.S. Ser. No. 08/367,705 filed Dec. 31, 1994; U.S. Ser. No. 08/535,585, filed Sep. 28, 1995 and U.S. Ser. No. 08/334,656, filed Nov. 3, 1994.

This application also is related to the following co-pending and commonly invented Provisional U.S. patent application Ser. No. 60/60/010,507, filed Jan. 24, 1996.

BACKGROUND OF THE INVENTION

1. Field of the Invention

This invention relates to surgical instrumentation and more particularly to instruments and methods for accomplishing a minimally invasive saphenous vein removal or for harvesting portions of other veins for bypass grafting elsewhere in a patient's body.

2 Description of Prior Art

Saphenous veins often are harvested for use in cardiac bypass grafts (CABG) and other peripheral vascular graft procedures. Typically, an open form of surgery is utilized which includes one or more long incisions between the patient's groin and ankle. The surgeon sharply dissects the vein away from surrounding tissues and divides the branch veins extending away from the main vein. Such open vein harvesting procedures are time-consuming and result in disfiguring scars. Further, such open procedures cause significant post-operative pain and often result in post-operative infections. Therefore, new instruments and methods are needed for performing a saphenous vein removal utilizing minimally invasive surgery (MIS) techniques.

SUMMARY OF THE INVENTION

In general, the present invention provides a 360° vein dissection instrument and method (i) and for accomplishing a blunt dissection of connective tissues in 360° around a saphenous vein, (ii) for transecting branch veins extending away from the saphenous vein, and (iii) for removing the vein from the body. The dissection instrument is described herein with reference to the exemplary method of harvesting a saphenous vein, but may be utilized for removal of other veins or similar structures.

The 360° pulsable tissue-plane dissector has an elongate body made of any slightly flexible material, such as a medical grade plastic. A distal region of the dissector body is formed into circumferential dissecting portion having a slanted distal termination of about 20°. The circumferential dissecting portion is progressively "circumferential" or "wrapped" around an axial vessel-receiving passageway or channel. The dissecting portion further defines a longitudinal-extending gap serving two purposes. First, the main vein may be disposed in the vein-receiving passageway through the gap. Second, the gap has a reduced transverse dimension in the proximal direction and serves as a "funnel" to funnel branch veins through the gap for dissecting tissues away from branch veins. Wing portions of the circumferential dissecting portion on either side of the longitudinal gap preferably are of resilient material and may deform under tissue pressure to further close the gap.

The circumferential dissecting portion further includes an "active" periphery incorporating a pulsable expansion structure of elastomeric material. An inflation lumen is formed in the dissector body to deliver an inflation medium to a pressurizable chamber within the expansion structure. A pressure source including a pulse-control mechanism is provided such that a single pulse will move the expansion structure in a "pulse cycle", i.e., through an "expansion phase" and a "contraction" phase. The pulse control mechanism provides pulse cycles ranging from 1 per second to 100 per second, preferably 1 per second to 50 per second, and more preferably between 5 and 20 per second. A foot pedal or other trigger is provided to actuate the pulse-control mechanism. In one embodiment, endoscopic viewing means in the form of a removable endoscope are provided with the body of the dissector.

In a method of the present invention to a circumferentially dissect around a saphenous vein, e.g., in a patient's thigh, the surgeon makes an incision near the patient's knee and exposes the saphenous vein. Such a saphenous vein portion typically has several branch veins branching away from the main vein, each branch vein having a circuitous form near the main vein. The surgeon axially advances the distal tip of the dissector into the plane between the surface of the vein and surrounding tissue layers. The surgeon places the circumferential dissecting portion of the dissector around the vein by slipping the vein through the longitudinal gap and into the vessel-receiving passageway.

With the vein in the vessel-receiving passageway and the circumferential dissecting portion thus partially around the vein, the surgeon actuates the trigger causing the expansion structure pulse through its "expansion" and "contraction" phases in rapid pulse intervals. Such rapid pulsation of the elastomeric structure facilitates the distal advancement of the dissector along and within the natural plane around the vein. The pulsed elastomeric structure rapidly stretches, disrupts and severs connective tissues in the natural plane around the vein thus creating an atraumatically and bluntly dissected space. With the expansion and contraction phases timed at from 5 per second to 20 per second, the disruption and dissection of connective tissues occurs very rapidly. The surgeon applies a constant axial pressure on the instrument, and the instrument easily can be advanced axially in the fractions of a second that the viscoelastic tissue layers on either side of the plane are separated and maintained apart by inertia.

The surgeon advances the dissector while continuing pulsation of the elastomeric expansion structure and at the same time angularly rocks the instrument. Contemporaneously, the surgeon may view the dissected space through the endoscope via the video monitor. Branch veins are straightened or stretched as they pass along the longitudinal gap into the narrowed proximal end of the gap. The pulsation of the expansion structure portion along the narrowed gap also dissects branches away from surrounding tissues.

Thereafter, the surgeon utilizes an accessory instrument (e.g., a bi-polar scissors) inserted into the dissected space to transect the branch veins, preferably about 1 mm. to 3 mm. away from the main vein. Finally, the surgeon cuts the vein at each end (e.g., at a knee incision and a groin incision) and pulls the vein segment from the patient for use as a bypass graft elsewhere in the patient's body.

In an alternative embodiment of dissector, the circumferential dissecting portion of the instrument includes branch-transecting means incorporated into the dissector body for automatically dividing branch veins. For example, the circumferential dissecting portion has vein-transecting bi-polar electro-cautery electrodes along interior opposing faces of the dissector body along the longitudinal gap. A sharp blade also may be carried in the proximal end of the longitudinal gap to divide veils of tissue or branches falling within the gap that are not divided adequately by the electro-cautery electrodes.

The alternative embodiment also includes an elastomeric expansion structure that has an "everting" or "unrolling edge" characteristic. That is, the expansion structure has an inner element and an outer element that are divided by elastomeric web portion. Thus, the inner and outer elements "evert" or "unroll" during the expansion phase of a pulse cycle and thus unroll against tissue layers on either side of the natural plane being dissected which reduces friction between the expansion structure and the tissue layers. The alternative embodiment also may be adapted to be advanced blindly, without endoscopic vision.

In general, the present invention advantageously provides instruments and methods for extraluminally dissecting connective tissues in 360° around the exterior of an elongate anatomic structure such as a saphenous vein, where there exists a natural anatomic plane susceptible to blunt dissection. The invention also provides instruments and methods for dissecting around branch vessels that branch away from a main vessel.

The present invention advantageously provides an instrument with a pulsable elastomeric structure disposed around its distal periphery for bluntly dissecting connective tissues in a natural plane between tissue layers. Also provided is an instrument that has a circumferential or vein-wrapping portion for dissecting in 360° around the exterior a vein.

The present invention also provides an instrument with a pulsable elastomeric structure for dissecting connective tissues along lines of least resistance in a natural anatomic plane to create an atraumatic dissection.

Also provided is an instrument with a pulsable elastomeric structure that has an everting- or unrolling-type edge adapted for reducing friction as it dissects connective tissues within a natural anatomic plane.

The present invention advantageously provides an instrument with bi-polar electro-cautery electrodes disposed in a longitudinal gap for automatically transecting branch vessels captured in the gap as the instrument is advanced around a saphenous vein.

The present invention also provides an instrument with endoscopic viewing means disposed therein for viewing the dissection of connective tissues around a vein.

The present invention provides an instrument that is inexpensive and disposable. Additional advantages and features of the present invention appear in the following description.

BRIEF DESCRIPTION OF THE DRAWINGS

FIG. 4 is an enlarged perspective view of the elastomeric structure along a portion of the boundary of the dissector of FIG. 1.

DESCRIPTION OF THE PREFERRED EMBODIMENT

1. Type "A" 360° Pulse Dissector.

Figure 1:
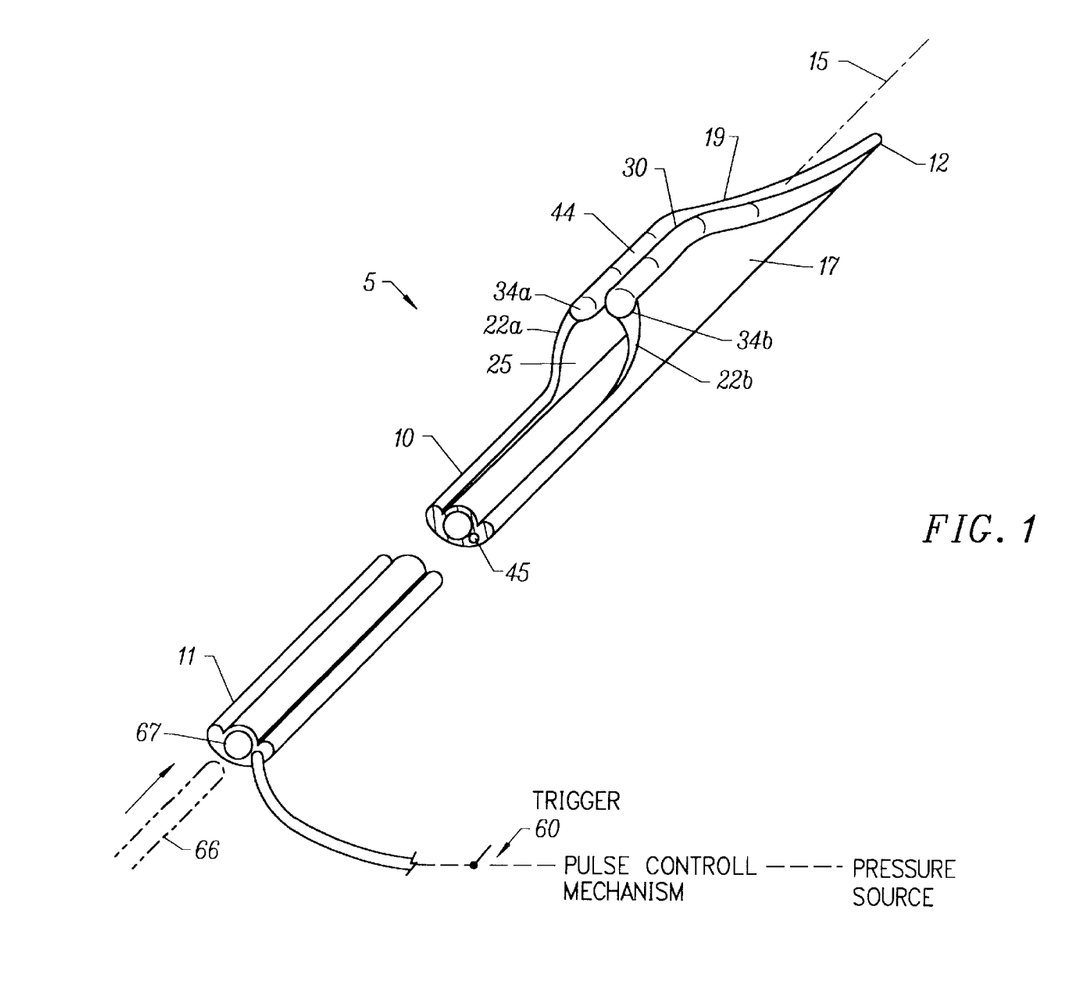
FIG. 1 is an axionometric view of a Type "A" 360° pulse dissector of the present invention.

By way of example, FIG. 1 illustrates 360° tissue-plane pulse dissector 5 adapted for atraumatic MIS harvesting of a saphenous vein. More in particular, FIG. 1 depicts elongate dissector body 10 having proximal end 11 and distal tip 12. Dissector body 10 extends alongside longitudinal axis 15 of the instrument. Body 10 is made of any suitable rigid or slightly flexible material, such as a medical grade plastic, a metal or a composite thereof (e.g., a medical grade stainless steel encased in a plastic such as Teflon).

Figure 2:
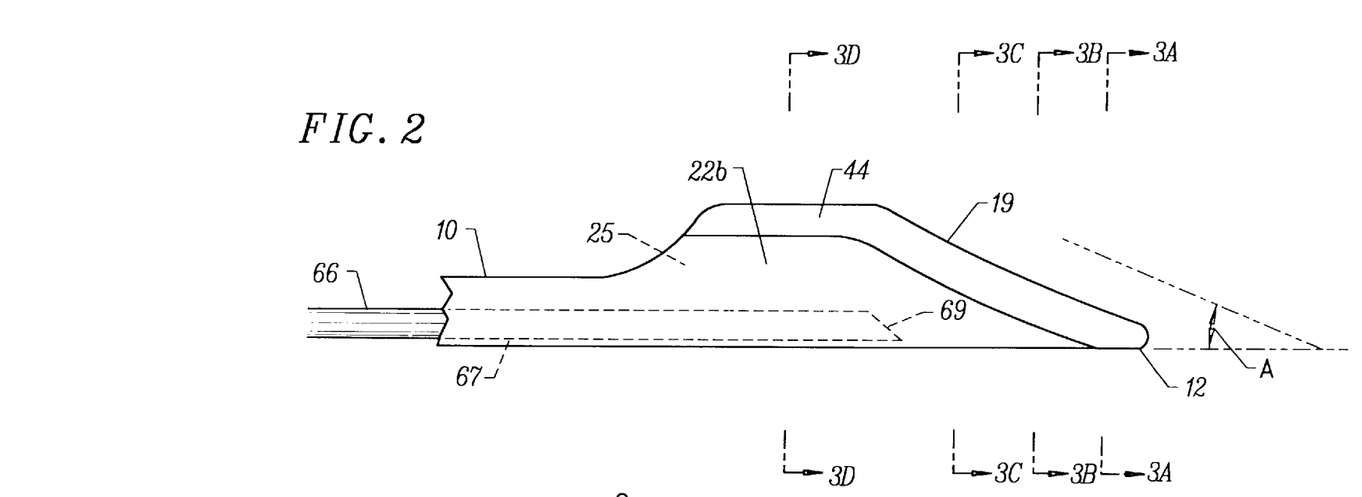
FIG. 2 is a longitudinal sectional view of a portion of the dissector of FIG. 1 taken along line 2—2 of FIG. 1.

As can be seen best in FIG. 1, a distal region of dissector body 10 is formed into "vein-wrapping" portion or circumferential dissecting portion 17 which has a particular longitudinal sectional shape (FIG. 2) as well as particular transverse sectional shape (FIGS. 3A–3D). FIGS. 2 and 4 show dissecting portion 17 having a slanted distal leading edge or periphery 19 (in longitudinal sectional view) with slant angle "A" ranging from 10° to 75° relative to axis 15, with such a leading edge or distal periphery 19 depicted in FIGS. 1–2 of about 20°. It should be appreciated that such distal periphery 19 also may have a curved contour (in longitudinal section) rather than a flat sectional contour.

As shown in FIGS. 2 and 3A–3D, circumferential dissecting portion 17 exhibits a substantially thin-wall element 20 that is progressively "circumferential" or "wrapped" around axis 15 with wing portions 22a and 22b substantially wrapping axis 15 to provide vessel-receiving passageway or channel 25. The cross-sectional dimension of channel 25 (FIG. 3D) is indicated by dimension "B" and may range from approximately 4.0 mm. to 15.0 mm. and preferably is from 5.0 mm. to 10.0 mm. The length of circumferential dissecting portion 17 may range from 10.0 mm. or less to 100.0 mm. or more.

Figure 3A:
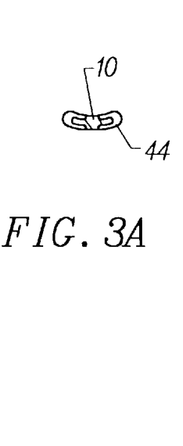
FIGS. 3A–3D are enlarged sectional views of a portion of the dissector of FIG. 1 taken along line 3A—3A, 3B—3B, 3C—3C and 3D—3D of FIG. 2 depicting the transverse sectional shapes of the dissector.
Figure 3B:
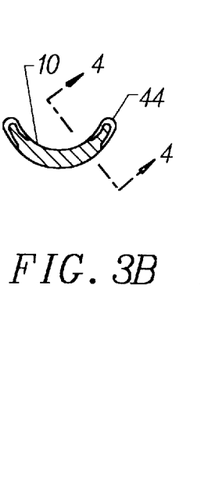
Figures 3C, 3D:
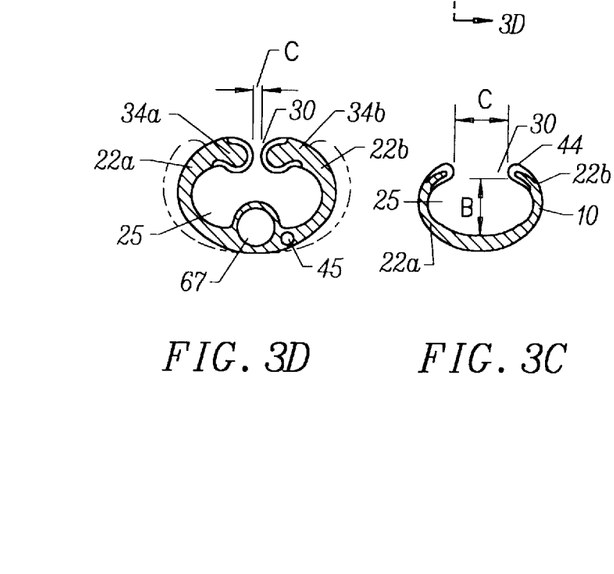

As can be seen in FIGS. 1 and 3C–3D, circumferential dissecting portion 17 progressively defines longitudinal-extending gap 30 for passing a main vein therethrough in the method of the present invention as described below. Gap 30 has a transverse gap dimension "C" that diminishes in the proximal direction thus serving as a funnel means for funneling branch veins through the narrowed proximal portion of the gap. FIGS. 3C–3D also show that gap 30 is circumscribed by opposing first face 33a and second face 33b. The opposing faces have an increased radius or rounded forms 34a and 34b in the proximal part of dissecting portion 17 for dissecting connective tissues around branch veins as will be described below. Gap 30, and more particularly wings, 22a and 22b, on either side of gap 30 preferably are of resilient material and may deform under tissue pressures as shown in phantom view of FIG. 3D.

Figure 4A:
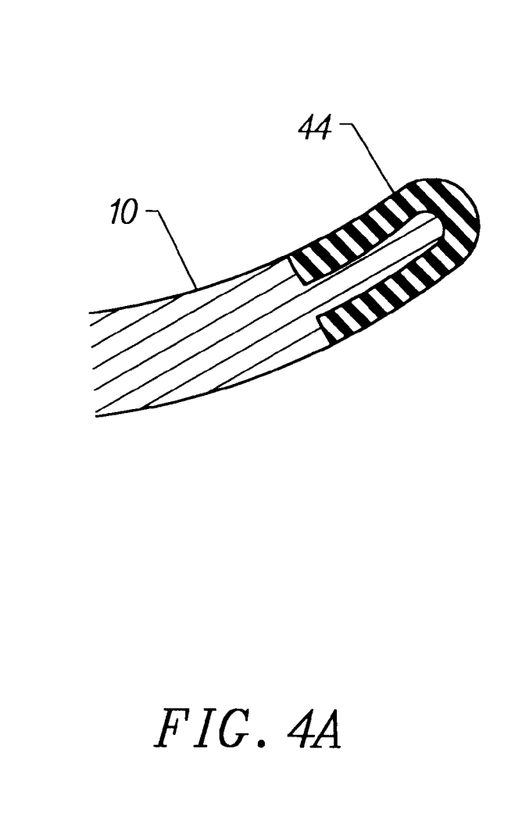
FIGS. 4A–4B are enlarged sectional views of the elastomeric structure, similar to a view taken along line 4—4 of FIG. 3B, in a contracted state and an expanded state.
Figure 4B:
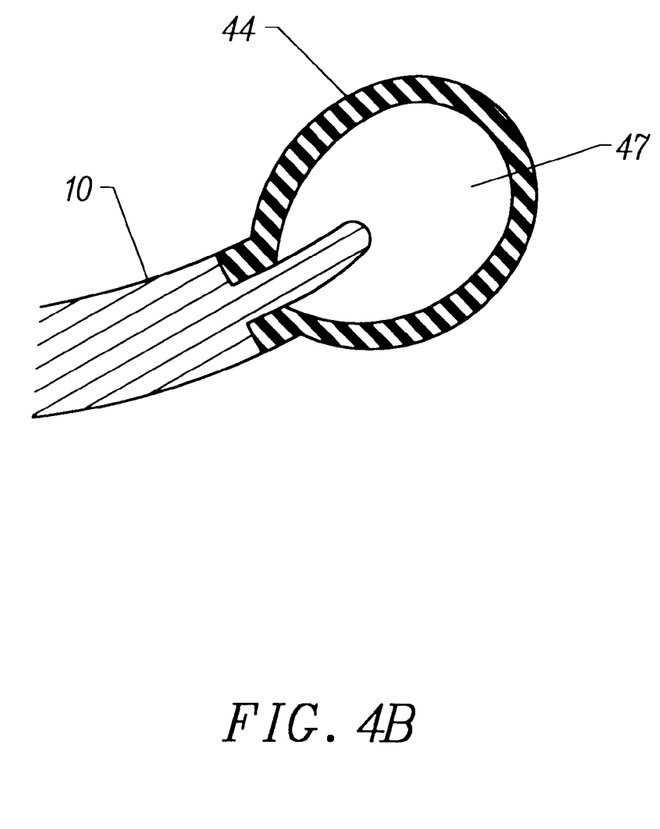

Referring now to FIGS. 1, 2, 4A and 4B, circumferential dissecting portion 17 further includes an "active" periphery 40 (or perimeter) by which is meant that pulsable expansion structure 44 of elastomeric material is incorporated along the distal leading edges 19 of dissecting portion 17. As can be seen in FIGS. 1 and 3D, inflation lumen 45 is formed into the dissector body 10 to deliver an inflation medium, such as air, $CO_2$, or a liquid to pressurizable chamber 47 within expansion structure 44. FIGS. 4A–4B illustrates sectional views of expansion structure 44 in a contracted state and an expanded state. A pressure source 50 is provided to pressurize chamber 47. Pressure source 50 further includes pulse-control mechanism 55 wherein a single pulse of the inflation medium within chamber 47 will move expansion structure 44 in a "pulse cycle." A pulse cycle herein means an "expansion phase" (from contracted state (FIG. 4A) to expanded state (FIG. 4B)) and a "contraction" phase (from expanded state (FIG. 4B) to contracted state (FIG. 4A)). Pulse cycle may range from 1 per second to 100 per second, preferably in the range from 1 per second to 50 per second, and more preferably are in the range of from 5 per second to 20 per second. Such a pulse-control mechanism 55 may comprise a peristaltic-type pump as disclosed in co-pending application Ser. No. 08/334,656. Alternatively, the pulse control mechanism may be any suitable pump that operates to provide an inflow pulse and an outflow pulse, such as a piston pump or a diaphragm pump. Alternatively, a pulse control mechanism may use a pressure source regulated by computer-controlled solenoid valve to time an inflow pulse together with a vacuum source regulated by computer-controlled cooperating solenoid valve to provide an outflow pulse, thus providing the desired pulsation effect.

The material of expansion structure 44 preferably is a suitable elastomeric material such as latex, silicone or urethane. The wall thickness of the elastomer may range from 0.005" to 0.015" depending on the dimensions of the structure and pressure characteristics of the pressure source. Thus, the psi generated by the pressure source may range from 10.0 psi to 150.0 psi or more. Alternatively, the durometer or strength of the elastomer will be responsible for, or contribute to, the evacuation of the fluid medium from chamber 47 during the "contraction" phase of the pulse cycle of expansion structure 44. Expansion structure 44 may be fixed to body 10 by any suitable means such as adhesives.

The amplitude or amount inflation medium comprising each pulse depends on the volume of chamber 47 and may range from less than 0.05 cc. to 5.0 cc. or more. As described above, any type of pulse control mechanism 55 may include a vacuum source for evacuating, or assisting in the evacuation of, the inflation medium from chamber 47. In the rapid pulse cycles described above, e.g., from 5 to 20 pulses/second, it is preferable to use a liquid inflation medium rather than a gaseous medium. The effect of transmitting "dissecting energy" by a pulsing expansion structure to a dissectable natural plane between tissues layers (as described below) with a gas will be lessened by the compression and decompression of a gas. A liquid is not susceptible to compression and thus will transmit greater dissection energy to the target plane.

FIG. 1 schematically shows trigger 60 for pulse-control mechanism 55 located in a foot pedal, but it should be appreciated that a trigger may be in a proximal portion of dissector body 10 for finger actuation or another suitable location. Also, it should be appreciated that a variable speed control (not shown) for pulse-controller 55 may be provided which will allow the surgeon to selectively control the number of pulses per second within the preferred ranges described above. For example, in the peristaltic-type pulse controller of U.S. Ser. No. 08/334,656, the pulse speed is controllable simply by selectively setting the speed of rotation of the peristaltic pump shaft.

The medial portion 64 of dissector body 10 has a linear form and extends alongside axis 15 from 300.0 mm. to 500.0 mm. or any other suitable length for dissecting along and around a saphenous vein or other blood vessel, e.g., for harvesting a portion of saphenous vein in a patient's thigh. The medial portion 64 may be somewhat flexible in bending but resistant to torsional forces for performing the method described below. The distal tip 12 of dissector 10 is blunt and rounded for bluntly dissecting a path within a tissue plane along and around the exterior of a saphenous vein. As can be seen in FIGS. 1 and 3A–3D, dissector body 10 increases in transverse sectional dimension in the proximal direction from tip 12 to the more middle section 65 of circumferential dissecting portion 17.

FIG. 1 shows that endoscopic viewing means are disposed within dissector body 10 for viewing around the circumferential dissecting portion 17 which comprises a conventional straight endoscope 66 (e.g., 3 mm. to 5 mm. diameter) disposed in axial bore 67. Endoscope 66 is connected conventionally to video monitor 68. Endoscope 66 is shown in phantom view with a 45° lens 69. It should be appreciated that any diameter scope, whether rigid or flexible, may be suitable and various angled lens may be appropriate depending on the location of the lens relative to the circumferential dissecting portion 17. Alternatively, endoscopic fiber optics may be built into dissector body 10 (not shown).

2. Operation of Type "A" 360° Pulse Dissector.

The use of Type "A" dissector 5 of FIG. 1 in performing a method of the present invention now may be described in the 360° dissection of saphenous vein 70 away from surrounding tissue layers 71 and in the removal of the vein portion from the patient's body as shown in cartoons and axionometric views of FIGS. 5A–5E.

Figure 5A:
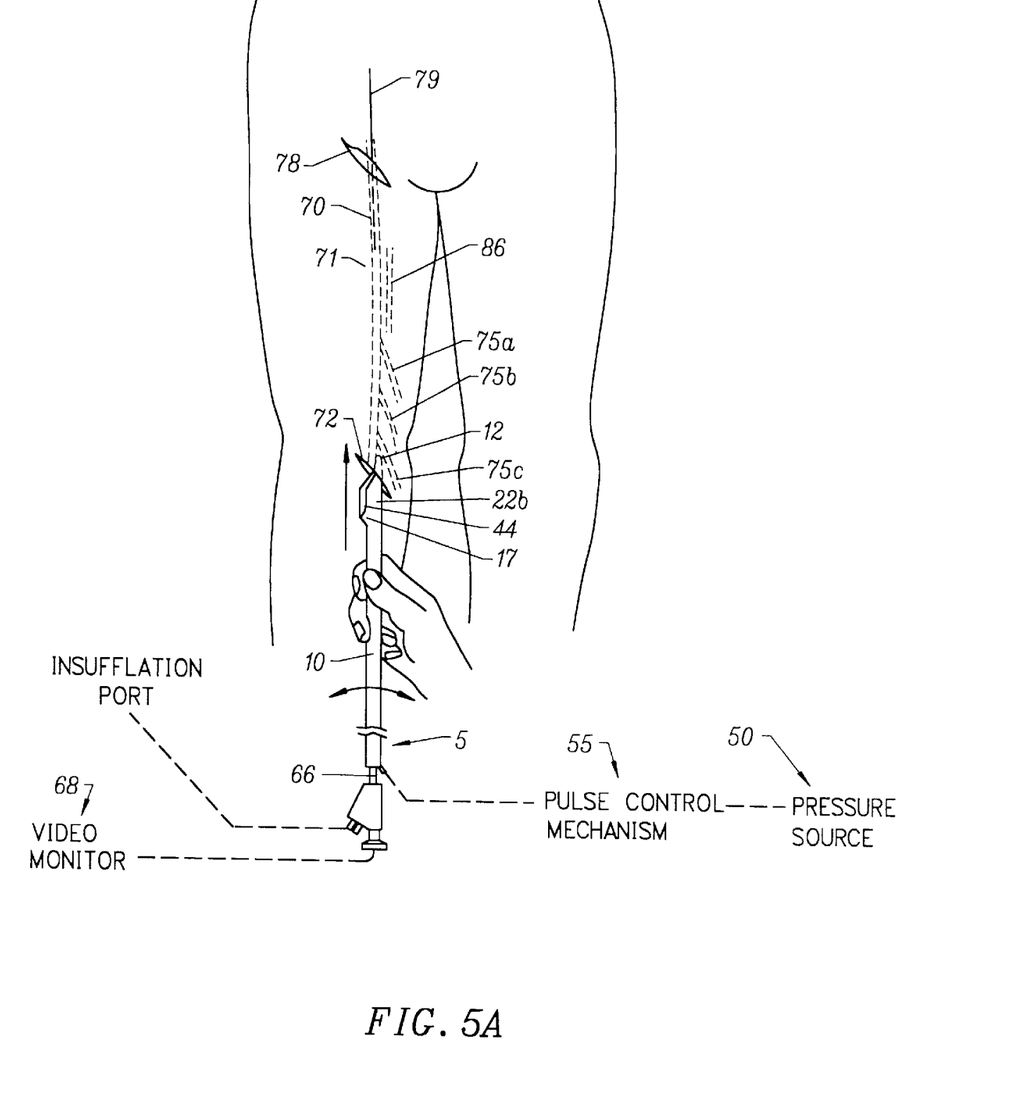
FIGS. 5A–5E are a sequence of cartoons, sectional of FIG. 7, in contracted, intermediate expanded and fully expanded states.
Figure 5B:
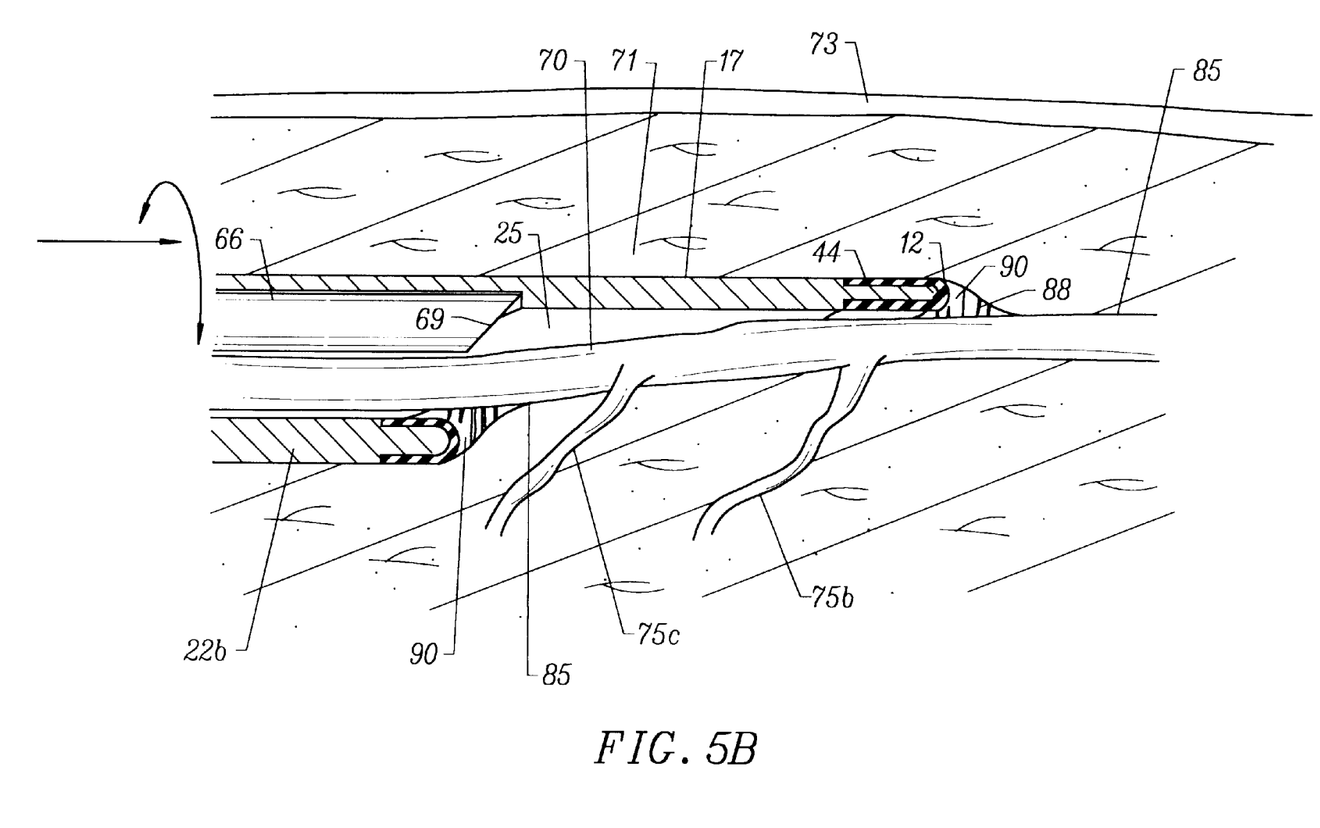

Referring to FIG. 5A, the surgeon makes incision 72 through skin layer 73 and other tissue layers near the patient's knee and exposes saphenous vein 70. A saphenous vein in a thigh typically may have from ten to twenty or more small branch veins circuitously branching away from the main vein 70, which branches are indicated herein as numbering only three, i.e., branch veins 75a, 75b and 75c. The saphenous vein is subcutaneous and such branch veins 75a–75c typically extend deep into the interior of the patient's leg. The branch veins intersect with main vein 70 typically from its interior aspect, or about 180° or less around such posterior interior, leaving the anterior aspect of vein 70 generally free from branches to provide a track for the tip 12 of dissector 5 to follow. The surgeon then (optionally) makes incision 78 in the patient's groin to expose vein 70. As can be seen in FIGS. 5A–5B, vein 70 has a linear axis 79 in the patient's leg.

Referring to FIGS. 5A–5B, the surgeon retracts skin 73 and tissue around knee incision 72 and then axially advances distal tip 12 of dissector 5 into plane 85 (FIG. 5B) between the anterior surface of vein 70 and surrounding tissue layers 71, which may include between the vein and any nerve 86 or other structure adjacent to the vein (see FIG. 5A). As shown in FIG. 5B, the surgeon places circumferential portion 17 of the dissector substantially around vein 70 by slipping the vein through gap 30, thus disposing vein 70 in vessel-receiving passageway 25 (FIG. 5B). The surgeon may slip vein 70 into passageway 25 most easily by using a wing portion (22a or 22b) to bluntly dissect around a portion of the vein as with any blunt dissection instrument, e.g., utilizing back-and-forth angular and axial movements. It should be appreciated that this method of disposing a dissector in substantially 360° around a vein does not require vein 70 to be transected initially, which is an improvement over the method of co-pending U.S. Ser. No. 08/367,705 which typically first required cutting an end of the vein.

With circumferential dissecting portion 17 around the vein 70 as shown in FIG. 5B, the surgeon actuates trigger 60 thus causing expansion structure 44 to be actuated in pulse cycles through its "expansion" and "contraction" phases in rapid intervals (see FIGS. 4A–4B and 5B). The rapid pulsation of structure 44 facilitates the distal advancement of circumferential dissecting portion 17 by lessening the axial force required to advance the instrument, since the pulsed expansion structure 44 bluntly dissects connective tissues 88 in plane 85 along lines of least resistance thus creating dissected space 90. Further, the pulsed expansion structure 44 expands along lines of least resistance to atraumatically dissect plane 85. Without wishing to be limited to any single theory for explaining the effectiveness of the pulsation of expansion structure 44 for the dissection of connective tissues 88, it is known that expansion structure 44 in its expansion phase stretches, disrupts and severs connective tissues 88 in plane 85 around vein 70. Further, it is believed that expansion structure 44 in its contraction phase causes connective tissues proximate to the just-dissected space 90 of plane 85 to collapse thus seeking a new equilibrium. It is believed that such connective tissues 88 then are more susceptible to disruption and dissection in a subsequent expansion phase of the expansion structure's pulse cycle. With the expansion and contraction phases generated at from 5 per second to 20 per second, the disruption and dissection of connective tissues 88 occurs rapidly to develop dissected space 90.

Of particular interest to the present invention, pulse control mechanism 50 preferably expands expansion structure 44 to its expanded state explosively, e.g., in a time of approximately 0.05 second, thus transmitting energy explosively against connective tissues 88 in plane 85. Similarly, the contraction phase of expansion structure 44 is fast, preferably less than 0.05 second. Again, without wishing to be limited by any theory, it is believed that the collapse of expansion structure 44 to its collapsed state in a time of less than about 0.25 second or less is substantially faster than the collapse of tissue layers 71 and vein 70 on either side of dissection plane 85, due to the inertia of viscoelastic tissues. This factor facilitates the slight back-and-forth rotation of the dissector as well as its distal advancement. The surgeon may apply a constant pressure on the instrument, and the instrument easily can be advanced in the fractions of a second that the viscoelastic tissues layers are separated and maintained apart by inertia.

Figures 5C, 5D:
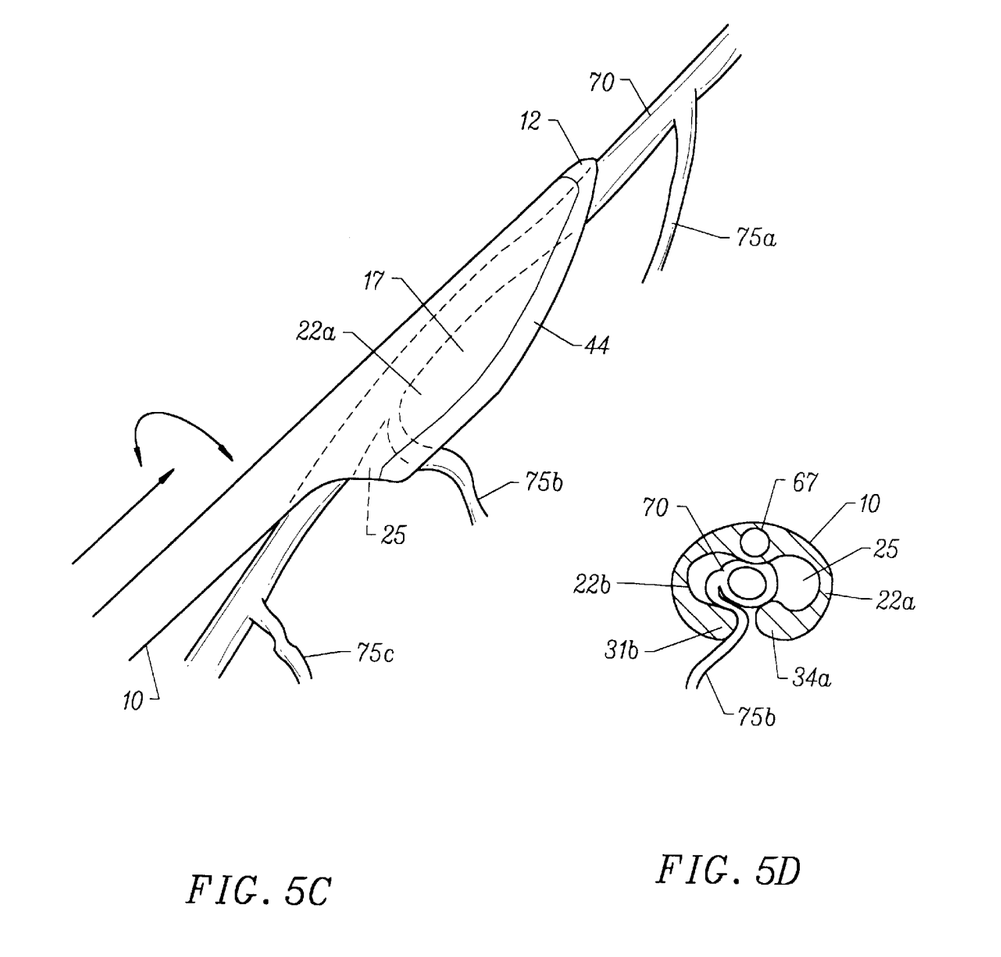

Referring to FIGS. 5B–5C, the surgeon then advances circumferential dissecting portion 17 distally while continuing pulsation of elastomeric structure 44. To facilitate advancement of the dissector, the surgeon slowly rotates and counter-rotates, or angularly rocks, the dissector while viewing through endoscope 66 via video monitor 68 (see FIG. 1). The angled endoscope lens generally affords a view around portions dissected space 90 as it is being dissected. Such angular movement of the dissector may range from 0° to about 90°. The back-and-forth angular rocking of the instrument accomplishes several objectives, displaying unique features of the invention. First, the advancement of dissector does not require the surgeon to grasp and re-grasp the dissector as in the spiral dissection methods disclosed in co-pending patent application Ser. No. 08/367,705 wherein helical advancement is utilized. Further, the back-and-forth angular rocking of the instrument under endoscopic vision allows the surgeon to view branch veins 75a–75c as the dissector is advanced. The surgeon thus may rotate the instrument in either direction further to insure that branch veins 75a–75c are funneled into and along the reduced dimension of gap 30. As can be seen in FIG. 5D, the branch veins are straightened or stretched from their circuitous form to an more elongate form as they pass through gap 30 and around rounded forms 34a and 34b. The pulsation of expansion structure 44 along gap 30 also dissects branches 75a–75c away from surrounding tissues.

Figure 5E:
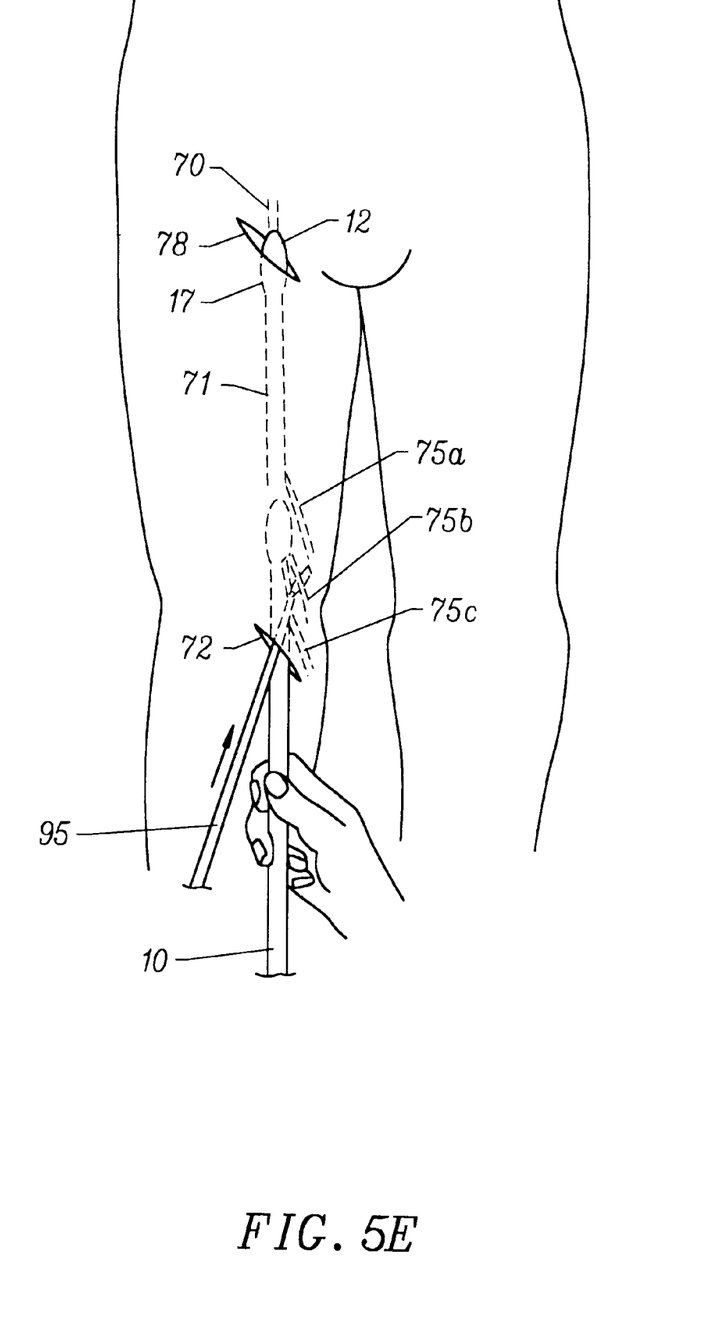

As can be seen in FIG. 5D, the rounded forms 34a and 34b along gap 30 insure that connective tissues 88 are dissected away from branch vein 75a a distance D away from vein 70, which is desirable. FIG. 5E shows the surgeon then utilizing an accessory instrument 95 (e.g., a bi-polar scissors or a vein-clipping device) introduced into dissected space 90 to transect the branch veins, preferably about 1 mm. to 3 mm. away from the main vein which is possible since rounded forms edges 34a and 34b dissected outwardly around the branch veins. The surgeon preferably stops the pulsation of expansion structure 44 while transecting branch veins. The surgeon may transect the branch veins as dissector 5 is advanced (see phantom view, FIG. 5E) or advance the instrument to groin incision 78 and thereafter transect the branch veins. After branch veins 75a–75c have been transected, the surgeon withdraws the dissector proximally, again preferably utilizing the pulsation of expansion structure 44, thus atraumatically mobilizing vein 70 relative to surrounding tissue layers 71. Thereafter, the surgeon cuts the vein at each end (knee incision 72 and groin incision 78) and may pull the vein segment from the patient's body if the vein is to be harvested for a bypass graft bypass elsewhere in the patient's body.

It should be appreciated that the method of the invention includes use of the vein segment for an in-situ reversed-flow bypass, wherein removal of the vein from the patient's thigh is not a step of the method. In such an in-situ bypass, it should be appreciated that other types of branch transecting and clipping instruments may be utilized, along with valvuatomes for cutting valves in the vein segment.

The step of removing the vein segment from the patient's body may be facilitated by insufflating the dissected space around the vein utilizing known procedures. For example, an insufflation lumen 97 in endoscope 66 (FIG. 5A) or an insufflation lumen (not shown) may extend through body 10 may be utilized to insufflate dissected space 90 around vein 70 contemporaneous with the atraumatic 360° dissection of the plane around the vein. Such an insufflated space may facilitate the transection or clipping of the branch veins by providing an improved or enlarged viewing space.

Alternatively, the step of removing the vein segment from the patient's body may be facilitated by using the enveloping sleeve disclosed in patent application Ser. No. 08/316,290 to isolate the vein in 360° as it is withdrawn from the patient's body.

In another respect, this method of the present invention is an improvement over the methods disclosed in co-pending U.S. patent application Ser. No. 08/535,585 in which an intraluminal stent element is introduced into the vein to make the vein more rigid. Still, it should be appreciated that an elongate inflatable intraluminal stent may be introduced into the vein portion to be harvested which may facilitate the extraluminal blunt dissection of connective tissues 88 with the dissector of the present invention. (See the elongate inflatable intraluminal stent disclosed in co-pending application Ser. No. 08/535,585). It further should be appreciated that instrument described above may be advanced from either direction (thigh-to-knee, knee-to-thigh) to accomplish the method of the present invention.

Thus, using the above method, the surgeon may accomplish an atraumatic extraluminal dissection of connective tissues in 360° around a saphenous vein, other blood vessel or other anatomic structure.

3. Type "B" 360° Pulse Dissector.

Figures 6, 7:
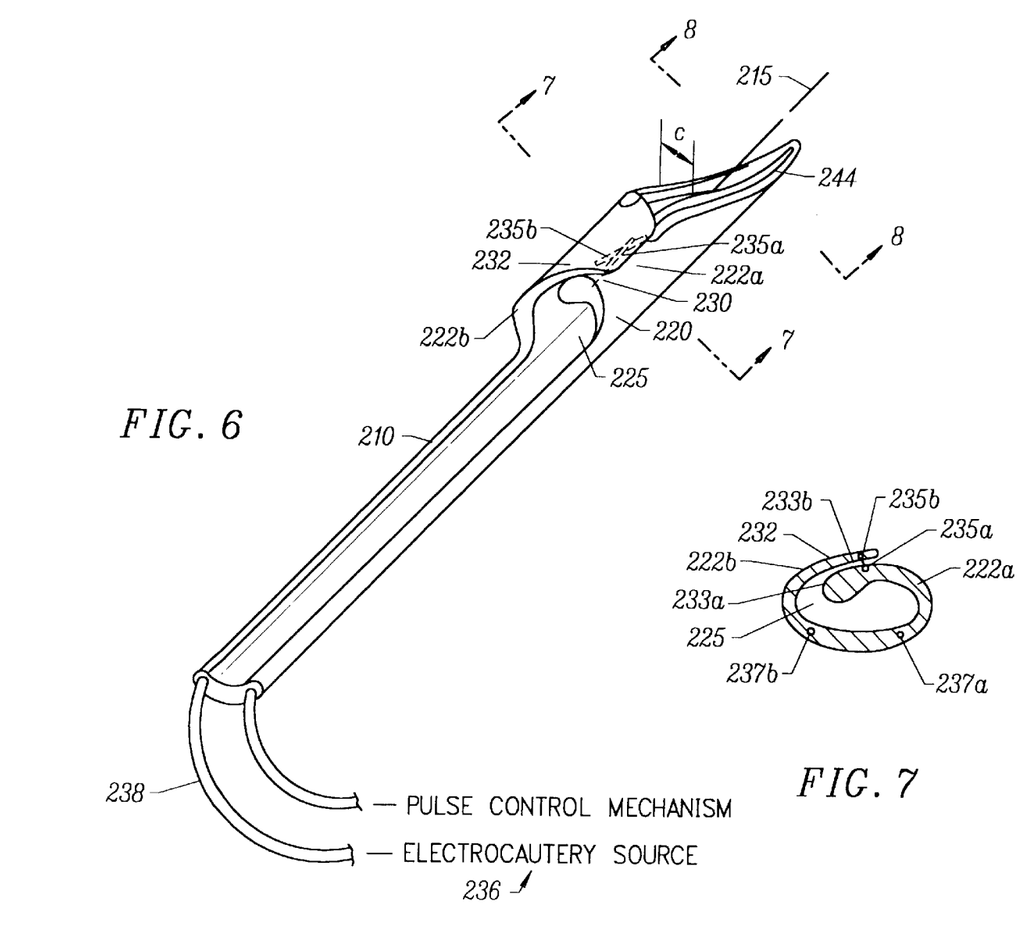

FIG. 6 illustrates 360° tissue-plane pulse dissector 205 adapted for atraumatic MIS harvesting of a saphenous vein. In the subsequent FIGS. 6 to 9, aspects of the Type "B" embodiment that compare to similar aspects of the Type "A" embodiment have similar reference numerals with the addition of 100. Like reference numerals of elements of the patient's body are utilized in the method of using the Type "B" embodiment.

Note that Type "B" dissector 205 has no endoscopic viewing means disposed therein and is suited for the blind dissection of vein segments. The Type "B" dissector 205 further differs from the first-described embodiment in that the alternative embodiment includes branch-transecting means incorporated into dissector body 210 for automatically dividing branch veins as the instrument is blindly advanced around and along a saphenous vein.

Figure 9:
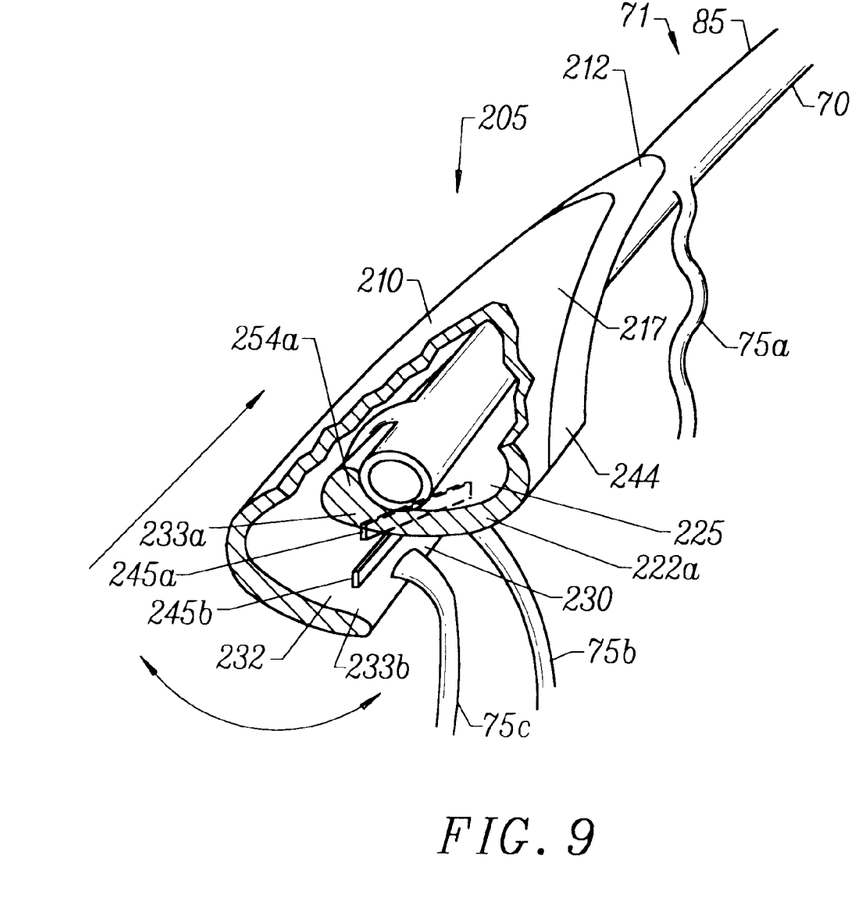
FIG. 9 is an axionometric view of a vein showing the manner in which the instrument of FIG. 6 is utilized to perform a dissection method of the present invention in harvesting a portion of a saphenous vein from the patient's thigh.

Referring to FIG. 6, circumferential dissecting portion 217 is of a thin-wall form 220 with wing portions 222a and 222b that wrap around axis 215. In this embodiment, wing portions 222a and 222b overlap substantially to define vein-receiving passageway 225 as well as gap 230. Gap 231 diminishes in transverse dimension "C" until the wing portions overlap in overlapping section 232. Opposing faces 233a and 233b then define gap 230 between the overlapping portion. Rounded form 234a is incorporated into wing 222a. Vein-transecting bi-polar electro-cautery electrodes 235a and 235b are positioned along gap 230 within overlapping portion 232, protected from contact with a vein in passageway 225 as well as tissue layers 71 around the circumference of dissecting portion 217. Each transecting electrode, 235a and 235b, is connected to electro-cautery source 236 by current-carrying wires 237a and 237b within body 20 (see FIG. 7). As can be seen in FIGS. 7 and 9, electrodes 235a and 235b may be canted slightly relative to one another so that no matter how the resilient parts of the dissector body overlap, the electrodes will cross each other. A sharp blade (not shown) also may be carried in the proximal end of gap 230 to divide any veils of tissue falling within the gap that are not divided adequately by the electro-cautery electrodes. For example, a blade may be of flexible stainless steel in thickness ranging from 0.002 to 0.010 similar to razor blade material. FIG. 7 shows electrical connector 238 that is removably plugged into the proximal end of body 210. The electro-cautery electrodes preferably remain in an "on" position during a vein dissection procedure, but it should be appreciated that a trigger (not shown) maybe provided to selectively actuate the electrodes between the "on" and "off" positions during use.

Figure 8A:
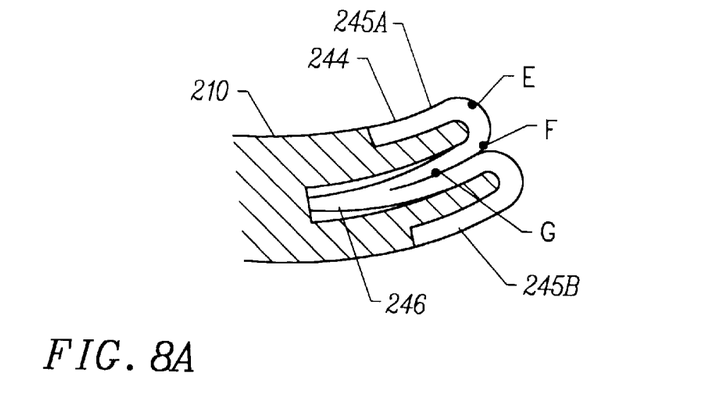
Figure 8B:
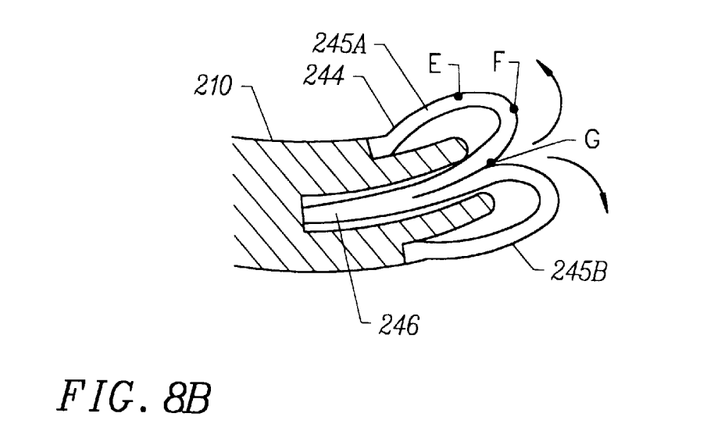
Figure 8C:
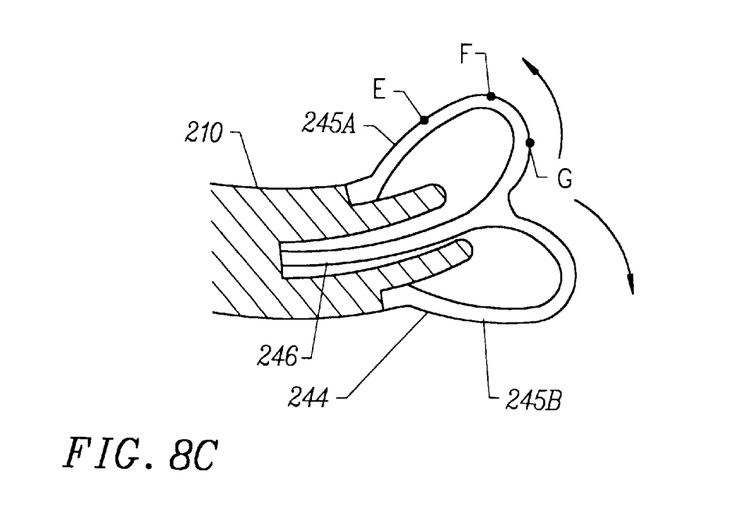

As can be seen in FIGS. 6–7, expansion structure 244 is similar to the first-described embodiment and is disposed around a distal periphery of circumferential dissecting portion 217. In this embodiment, expansion structure 244 extends proximally along edges of wing portions 222a and 222b. The sectional views of FIGS. 8A–8C show that expansion structure 244 has an "everting" or "unrolling" edge, by which is meant expansion structure 244 has inner element 245a and outer element 245b that are divided by elastomeric web portion 246. In FIGS. 8B and 8C, it can be seen that inner element 245a and outer element 245b unroll or evert during the expansion phase of a pulse cycle which desirably dissects connective tissues 85 in plane 80 by causing inner element 245a and outer element 245b to unroll against tissue layers on either side of tissue plane 80. Such an everting or unrolling characteristic reduces friction or the abrading effect between expansion structure 244 and the tissue layers as the pulse cycle is ongoing. (This differs from the Type "A" expansion structure 44 which does not "unroll" against a tissue layer, but expands and causes friction against the tissue layers on either side of plane 85 as the structure stretches). E.g., in FIGS. 8A–8C, it can be seen that points "E", "F" and "G" are equidistant along the surface of expansion structure 244, and that in the expansion phase, points "E", "F" and "G" unroll against tissue layer 71. Note that web portion 246 typically may have a reduced section or thickness to make it more elastic than inner element 245a and outer element 245b. Inner element 245a and outer element 245b may be substantially non-elastomeric in comparison to web 246.

4. Operation of Type I"B" 360° Pulse Dissector.

The use of Type "B" dissector 205 of FIGS. 6–7 in performing a method of invention is similar to the previously described method. For example, the surgeon makes an incision near the patient's knee and exposes a portion of a saphenous vein, again having branch veins 75a, 75b and 75c. The partial sectional view of FIG. 9 shows the surgeon advancing the distal tip of dissector 205 into plane 85 between the anterior surface of vein 70 and surrounding tissue layers 71. The surgeon disposes vein 70 in vessel-receiving passageway 225 as previously described. With circumferential portion 217 around vein 70, the surgeon actuates the trigger causing expansion structure 244 to actuate in pulse cycles through its "expansion" and "contraction" phases. The pulsation of structure 244 facilitates the distal advancement of circumferential dissecting portion 217, in particular by the everting or unrolling of the inner and outer elements 245a and 245b of expansion structure 244 as shown in FIGS. 8A–8C. Back-and-forth angular movement of the instrument, as previously described, allows the surgeon to progressively capture branch veins 75a–75c in gap 230 as the dissector is advanced. As the instrument is advanced further, the branches fall between opposing faces 233a and 233b in overlapping portion 232. The surgeon may rotate the instrument further to insure that branch veins slide along the reduced dimension of gap 230. As can be seen in FIG. 9, branch veins 75a–75c are straightened or stretched from their circuitous form to a more elongate form as they pass around rounded form 234a of wing 222a. The pulsation of expansion structure 244 along gap portion also dissects the branch veins away from surrounding tissues 71. The rounded form 234a thus insures that connective tissues are dissected away from branch veins 75a–75c a distance away from vein 70, which is desirable. FIG. 9 further depicts branch vein 75c being transected and cauterized by bi-polar electro-cautery elements 245a and 245b. Since branch vein 75c is stretched somewhat around rounded edge 234a, the branch will be transected preferably about 2 mm. to 3 mm. or more away from the main vein. After branch veins 75a–75c have been transected, the surgeon advances the dissector to the region of groin incision 78, again actuating the pulse control mechanism to pulse expansion structure 244. Thereafter, the surgeon cuts the vein at each end (knee incision 72 and groin incision 78) and may remove the vein, or prepare the vein for an in-situ by-pass, under the methods described above.

From the foregoing, it can be seen that instruments and methods are provided for atraumatically dissecting tissues in 360° around a vein. It can be readily seen that systems may manufactured in various special sizes, embodiments and lengths for dissecting and isolating various portions of a patient's arteriovenous system, e.g., for dissecting an entire length of a saphenous vein from the patient's groin to the ankle.

This disclosure is illustrative and not limiting. Although specific features of the invention are shown in some drawings and not in others, this is for convenience only and any feature may be combined with another in accordance with the invention and are intended to fall within the scope of the appended claims.

What is claimed is:

1. A surgical instrument for dissecting a natural tissue plane around a circumference of an elongate anatomic vessel to mobilize the vessel relative to surrounding tissues, comprising:
   a handle portion;
   an elongate body extending from said handle portion parallel to a longitudinal axis;
   a tissue-plane dissecting surface carried at a distal end of said elongate body, at least a portion of said dissecting surface having a cross-sectional shape that substantially wraps around said longitudinal axis thus defining an axial vessel-receiving channel;
   an expansion structure disposed around at least a portion of a periphery of said dissecting surface, said expansion structure movable between a contracted position having a lesser cross-sectional dimension and an expanded position having a greater cross-sectional dimension; and
   an expansion mechanism operatively connected to said expansion structure for actuating said expansion structure between said contracted and expanded positions.

2. The instrument of claim 1, further comprising a pulse-control mechanism operatively connected to said expansion mechanism for causing said expansion structure to move between said contracted and expanded positions in pulse intervals.

3. The instrument of claim 2, wherein the pulse intervals range from 1 pulse per second to 100 pulses per second.

4. The instrument of claim 1, wherein said tissue-plane dissecting surface defines at least one longitudinal gap means disposed therein (for capturing branches of said vessel therein).

5. The instrument of claim 4, further comprising:
   a longitudinal gap means having a transverse dimension that decreases in the proximal direction, and
   branch-transecting means disposed within a proximal portion of said gap means for transecting branches of said vessel.

6. The instrument of claim 5, wherein said branch-transecting means includes at least one electro-cautery means.

7. The instrument of claim 6, wherein said branch-transecting means includes a bi-polar electro-cautery means.

8. The instrument of claim 5, wherein said branch-transecting means includes a sharp blade element.

9. The instrument of claim 1, further comprising endoscopic viewing means within said elongate body for viewing around said dissecting surface.

10. The instrument of claim 1, wherein at least a portion of said dissecting surface wraps more than 360° around said longitudinal axis to overlap thereby defining an overlapping portion.

11. A surgical instrument for dissecting around a circumference of an elongate anatomic vessel to mobilize the anatomic vessel relative to surrounding tissues, comprising:
   an at least partially tubular body having a proximal handle portion and a distal dissecting portion, said body defining an axial channel extending therethrough for receiving said vessel;
   wherein said dissecting portion terminates in at least one longitudinally-projecting distal tip for penetrating tissue;
   at least one longitudinal gap means incorporated into said dissecting portion for receiving branches of said vessel, said gap means having a transverse dimension that decreases in the proximal direction; and
   branch-transecting means disposed within a proximal portion of said gap means for transecting said branches.

12. The instrument of claim 11, further comprising:
   an expansion structure disposed around at least a portion of a periphery of said dissecting portion, said expansion structure movable between a contracted position having a lesser cross-sectional dimension and an expanded position having a greater cross-sectional dimension; and
   an expansion mechanism operatively connected to said expansion structure for actuating said expansion structure between said contracted and expanded positions.

13. The instrument of claim 12, further comprising a pulse-control mechanism operatively connected to said expansion mechanism for causing said expansion structure move between said contracted and expanded positions in pulse intervals.

14. A surgical instrument for dissecting connective tissues within a natural anatomic plane in a patient's body, comprising, comprising:
   an elongate extension member extending along a longitudinal axis;
   an expansion structure incorporated around at least a portion of a distal periphery of said elongate extension member, said expansion structure movable between a contracted position having a lesser cross-sectional dimension and an expanded position having a greater cross-sectional dimension;
   an expansion mechanism operatively connected to said expansion structure for actuating said expansion structure between said contracted and expanded positions; and
   a pulse-control mechanism operatively connected to said expansion mechanism for causing said expansion structure move between said contracted and expanded positions in pulse intervals.

15. An instrument for dissecting connective tissues within a natural anatomic plane in a patient's body, comprising:
   an elongate body having proximal and distal ends and extending along a longitudinal axis;
   a dissecting portion carried at said distal end of said elongate body;
   an expansion structure disposed around at least a portion of a distal periphery of said dissecting portion, said expansion structure movable between a contracted position having a lesser cross-sectional dimension and an expanded position having a greater cross-sectional dimension;
   wherein said expansion structure is of a thin-wall flexible material, said expansion structure when viewed in cross-section having a first-side portion and a second side portion with an intermediate portion therebetween,
   said expansion structure when viewed in cross-section and when moving to said expanded state from said collapsed state, a first exterior surface of said first side and a second exterior surface of said second side move to said expanded position by unrolling distally thereby unrolling within said plane against tissues layer on either side of said plane thereby reducing friction and dissecting connective tissues in said plane; and an expansion mechanism operatively connected to said expansion structure for actuating said expansion structure between said contracted and expanded positions.

16. The instrument of claim 15, further comprising a pulse-control mechanism operatively connected to said expansion mechanism for causing said expansion structure to move between said contracted and expanded positions in pulse intervals.

17. The instrument of claim 14, wherein said expansion structure is of elastomeric material.

18. The instrument of claim 14, wherein said expansion structure is of non-elastomeric material.

19. The instrument of claim 14, wherein said expansion structure includes a fluid-tight inflation chamber.

20. A method for dissecting a natural plane around a circumference of a vessel having branches in a body of a patient to mobilize the vessel relative to surrounding tissues utilizing an elongate instrument with a circumferential distal working end having an expansion structure disposed around a periphery thereof, an actuator for actuating said expansion structure between contracted and expanded positions in pulses, and a longitudinal gap for capturing said branches, comprising the steps of;

making an incision in the body to expose a portion of said vessel in a first location;

pushing said distal working end into a tissue plane between the surface of said vessel and surrounding tissues in said first location;

disposing said circumferential working end substantially around said vessel;

actuating said actuator thereby causing said expansion structure to move between said contracted and expanded positions in pulse intervals;

advancing distally said working end to a second location remote from said first location thereby dissecting connective tissues in said natural plane;

transecting said branches with a branch-transecting means disposed in a proximal portion of said longitudinal gap thereby mobilizing said vessel relative to surrounding tissues.

21. The method of claim 20, wherein the advancing step includes the step of:

angularly rotating and counter-rotating said working end through an angle ranging from 0° to 180° thereby causing said periphery to dissect substantially in 360° around said vessel.

* * * * *